(12) United States Patent
Krill et al.

(10) Patent No.: US 6,265,617 B1
(45) Date of Patent: Jul. 24, 2001

(54) PROCESS FOR THE PREPARATION OF 3,5,5-TRIMETHYLCYCLOHEXA-3-EN-1-ONE (β-ISOPHORONE) BY ISOMERIZATION OF 3,5,5-TRIMETHYLCYCLOHEXA-2-EN-1-ONE (α-ISOPHORONE)

(75) Inventors: Steffen Krill, Speyer; Stephan Kretz, Biebergemund; Hans-Joachim Hasselbach; Klaus Huthmacher, both of Gelnhausen; Rainer Hahn, Budingen; Hermann Schmitt, Rodenbach, all of (DE)

(73) Assignee: Degussa-Huls Aktiengesellschaft, Hanau (DE)

( * ) Notice: Subject to any disclaimer, the term of this patent is extended or adjusted under 35 U.S.C. 154(b) by 0 days.

(21) Appl. No.: 09/310,971

(22) Filed: May 13, 1999

(30) Foreign Application Priority Data

May 13, 1998 (DE) .............................. 198 21 379

(51) Int. Cl.⁷ .................................................. C07C 45/00
(52) U.S. Cl. .......................................... 568/341; 568/347
(58) Field of Search ..................................... 568/341, 347

(56) References Cited

U.S. PATENT DOCUMENTS

| 2,246,032 | 6/1941 | Bent . |
| 3,397,120 | 8/1968 | Diana . |
| 4,010,205 | 3/1977 | Becker . |
| 4,026,948 | 5/1977 | Becker . |
| 6,005,147 | 12/1999 | Krill . |

FOREIGN PATENT DOCUMENTS

| 0 832 870 A1 | 4/1998 | (EP) . |
| 2 253 730 | 7/1975 | (FR) . |

*Primary Examiner*—Johann Richter
*Assistant Examiner*—J. Parsa
(74) *Attorney, Agent, or Firm*—Pillsbury Winthrop LLP

(57) ABSTRACT

A process for the preparation of 3,5,5-trimethylcyclohexa-3-en-1-one (β-isophorone) by isomerization of 3,5,5-trimethylcyclohexa-2-en-1-one (α-isophorone) in the liquid phase in the presence of a salt-like or organometallic catalyst. By using catalytic quantities of alkali-metal salts or alkaline-earth salts and/or their organometallic compounds, and without addition of a further auxiliary substance, the space-time yield in the preparation of β-isophorone is high. β-Isophorone is particularly suitable as an intermediate product for the preparation of ketoisophorone.

14 Claims, No Drawings

PROCESS FOR THE PREPARATION OF 3,5, 5-TRIMETHYLCYCLOHEXA-3-EN-1-ONE (β-ISOPHORONE) BY ISOMERIZATION OF 3,5, 5- TRIMETHYLCYCLOHEXA-2-EN-1-ONE (α-ISOPHORONE)

CROSS-REFERENCE TO RELATED APPLICATION

This application is based on German Application DE 19821379.4, filed May 13, 1998, which disclosure is incorporated herein by reference.

FIELD OF THE INVENTION

This invention relates to a process for the preparation of 3,5,5-trimethylcyclohexa-3-en-1-one (β-isophorone) by isomerization of 3,5,5-trimethylcyclohexa-2-en-1-one (α-isophorone) in the liquid phase in the presence of a salt-like catalyst containing an inorganic cation.

BACKGROUND OF THE INVENTION

β-Isophorone is of great interest economically because it is an important synthetic structural unit for the preparation of carotinoids, vitamins and pharmaceutical products. β-Isophorone in particular is necessary as a precursor for ketoisophorone (=2,6,6-trimethylcyclohex-2-en-1,4-dione) and trimethylhydroquinone and hence for the preparation of vitamin E. In addition, it plays a crucial part in syntheses of perfumes and natural substances such as astaxanthin and abscisic acid and derivatives.

Isophorone is prepared by trimerization of acetone, with condensation of the $C_3$ structural units. α-Isophorone is the main isomer formed because, unlike the β-isomer, it possesses a double bond conjugated to the keto function. For this reason, the thermodynamic equilibrium lies towards the α-isophorone; the β-concentration is only about 1–2%, depending upon the temperature, and the equilibrium is established very slowly.

Although there are in principle two different methods of obtaining ketoisophorone, namely, the direct oxidation of α-isophorone → ketoisophorone, and the detour via the isomerization of α-isophorone → β-isophorone in an initial step and subsequent oxidation of β-isophorone → ketoisophorone, the latter process is clearly more advantageous. Scheme 1 illustrates these observations on the synthesis of ketoisophorone:

Scheme 1
General principle of the synthesis of KIP
(= ketoisophorone = 2,6,6-trimethyl-2-cyclohexen-1,4-dione)

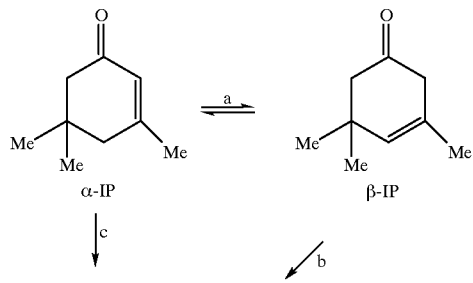

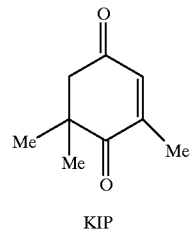

KIP a = isomerization of α-IP to β-IP
b = oxidation of β-IP to KIP
c = direct oxidation of α-IP to KIP Over the years numerous processes for the isomerization of α-IP have been described, which nevertheless have considerable disadvantages. Aspects such as high consumption of chemicals, poor space-time yield and problems during the working-up have hitherto prevented a practical transfer of the process to a larger scale.

In the processes for preparing β-IP from α-IP, a distinction can be made between gas-phase reactions and liquid-phase reactions.

Four parallel reactions of α-isophorone in the gas phase are possible in principle. These reactions compete with one another and succeed to a varying degree depending upon the selected temperature range and the surface condition of the catalyst employed.

In the gas phase, isophorone can react on contact in the following ways:

a) isomerization to β-isophorone b) reduction to trimethylcyclohexadienes (the hydrogen necessary for this is supplied through the decomposition of IP, which is accompanied by coking phenomena)

c) β-elimination of methane to 3,5-xylenol d) formation of mesitylene.

The catalyzed reactions of α-IP in the gas phase on a heterogeneous contact are shown in the following Scheme 2:

Scheme 2
Reactivity of α-IP in heterogeneous gas phase catalysis

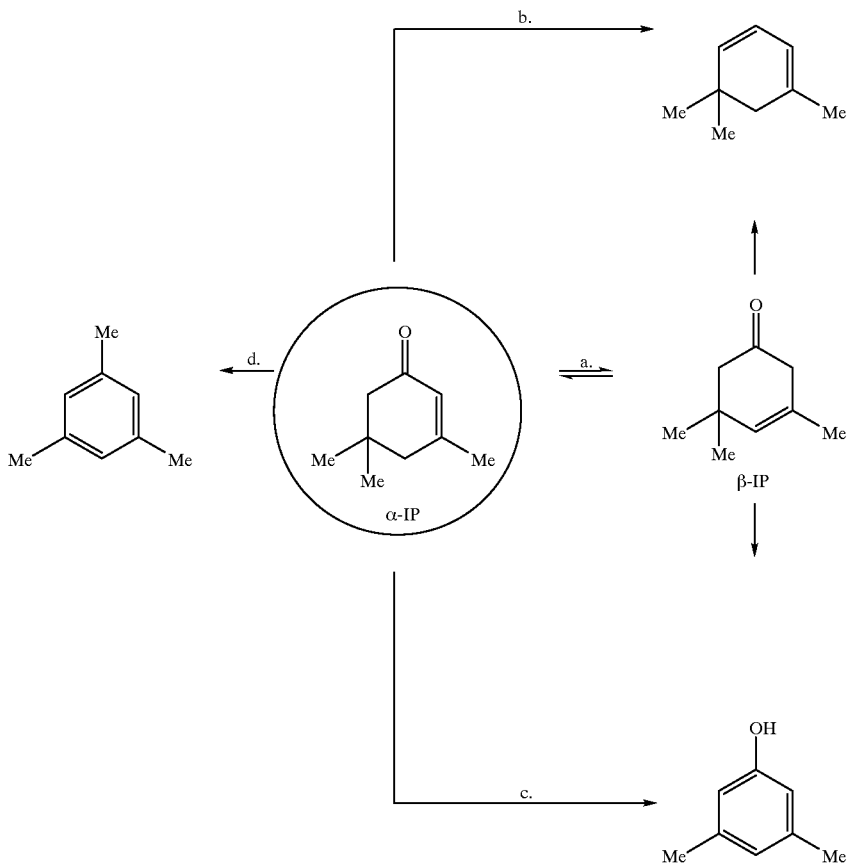

EP 0 488 045 B1 discloses an isomerization process in the gas phase (300–450° C.) above a heterogeneous catalyst. The catalysts used are oxides and mixed oxides of Mg (group IIa), Al (IIIa), Si (IVa) and Ni (VIII), which are active per se or are applied to a γ-aluminium oxide support (specific surface 1–50 m$^2$/g). 1–10 kg β-IP is used per liter of catalyst; the concentration of the solution obtained as intermediate is 9% β-IP at most, depending on the catalyst loading; the end concentration after distillation under vacuum is 97% β-IP. NiO is granulated using 1% Luviskol K90 (- polyvinylpyrrolidone). Under optimal conditions, a catalyst performance of 0.33 liter β-IP/h/liter$_{cat}$ is achieved when this procedure is employed. Based on the volume of educt used, the space-time yield $Y_{R-Z}$=0.09 liter$_{β-IP}$/h/liter$_{solution}$ (Ex. 1).

Moreover, the withdrawal rate is low, which renders the process less attractive on the industrial scale.

In L. F. Korzhova, Y. V. Churkin and K. M. Vaisberg, Petrol. Chem Vol. 31, 1991, 678 the reaction of α-IP at 300–800° C. in the presence of heterogeneous catalysts is described. The catalytic systems considered are γ-aluminum oxide, magnesium oxide and quartz. The range of products is examined in relation to temperature and catalyst. The formation of β-IP, trimethylcyclohexadiene, 3,5-xylenol and of mesitylene are compared with one another (see Scheme 2: routes a., b., c.; d.). Thus the thermal decomposition of α-IP at above 550° C. on a less developed catalytic surface (quartz) yields a mixture having the composition c>>a>>d and b=0. The reaction on the MgO contact at 400° C. shows a similar range of products at a significantly lower temperature, namely c>>a>d>b. In the presence of an aluminium oxide catalyst having a marked basic-acidic surface structure, the reaction takes place at 300° C. with a clear preference for the cyclohexadiene products, namely b>>c>d.

Altogether, it can be assumed that a catalytic gas phase isomerization as several quite definite disadvantages: in general, it can be said that these processes are disadvantageous because either the formation of the product is accompanied by a considerable accumulation of secondary products, or the space-time yield (absolute β-IP-formation/h/kg$_{cat}$) is too low.

There are also a number of publications which deal with the isomerization in the liquid phase. The closest prior art is represented by the following documents:

D1=A. Heymes et al., Recherches 1971, 18, 104
D2=FR-A-1 446 246
D3=DE-OS-24 57 157
D4=U.S. Pat. No. 4,005,145
D5=EP-A-0 312 735
D6=JP87-33019 eq. to HEI-1-175954 v. 12.07.1989

D1 discloses the isomerization of (α-IP to β-IP using stoichiometric quantities of MeMgX (X=halogen-), a Grignard compound. In the presence of catalytic quantities of FeCl$_3$, 73% β-IP is obtained, with release of methane. Mechanistic concepts assume that the Grignard compound reacts as a base and does not function as the carrier of a carbanion. Excess Mg leads to the formation of mixtures of dimers, which are the result of a reducing metallic dimerization. However, the reaction of α-isophorone with molar quantities of methylmagnesium iodide in the presence of catalytic quantities of FeCl₃, the subsequent hydrolysis and the working-up by distillation is a complicated procedure as well as being expensive as regards chemicals.

D2 relates to the isomerization of α-IP to β-IP in the presence of catalytic quantities of p-toluenesulfonic acid and aromatic sulfonic acids generally, in particular anilinesulfonic acid. The quantity of the catalyst used is 0.1–0.2%, based on the α-IP used. However, a lower degree of conversion and a greater accumulation of secondary products prevents an industrial application of the process in D2.

According to D3, β-IP is prepared by boiling α-IP for several hours in triethanolamine, fractionating and then washing the distillate with tartaric acid and common salt solution. Again, the consumption of chemicals and the labor expended in the process are considerable.

In D4, acids having a pK=2–5 and a boiling point higher than that of β-IP (bp β-IP=186° C./760 mm Hg) are used as catalyst. The patent claim explicitly protects the following compounds in the liquid phase:

aliphatic and aromatic amino acids, adipic acid, p-methylbenzoic acid, 4-nitro-m-methylbenzoic acid, 4-hydroxybenzoic acid, 3,4,5-trimethoxybenzoic acid, vanillic acid, 4-trifluormethylbenzoic acid, 3-hydroxy-4-nitrobenzoic acid and cyclohexanecarboxylic acid and derivatives.

The quantity of catalyst used is 0.1–20 mol.%. The yield of β-IP (based on α-IP used) and therefore the selectivity is 74.5%. Under the given conditions this corresponds, converted to the quantity of catalyst used and time, to a yield Y=0.218 liters β-IP per kilogram of catalyst per hour.

The homogeneous catalytic isomerization of α-IP to β-IP accompanied by little dissociated acid is an improvement as regards the consumption of chemicals, with β-IP being continuously removed from the equilibrium. With a withdrawal rate as low as 11 ml/h β-IP at an input of about 0.5 kg α-IP, the space-time yield and the formation of β-IP has a value Y=0.24 kg β-IP/kg$_{cat}$/h, which is too low for industrial application.

A similar principle is followed in D5. Acetylacetonates of transition metals are used as catalysts for shifting the π bonds. Al(acac)₃ also exhibits catalytic activity. The catalyst is used in a quantity of 0.01–10 wt %. The catalysts patented are metal catalysts of the groups IVb (Ti/Zr/Hf), Vb (V/Nb/Ta), VIb (Cr, Mo, W), VIIb (Mn/ Tc/Re), the whole of group VIII and aluminum. The primary distillate obtained has a β-IP content of 94%, a further Vigreux distillation concentrates the β-IP content to 99%. Based on the quantity of catalyst used and the time, this result corresponds to a yield Y=9.4 liters β-IP per kilogram of catalyst per hour. Based on the educt solution used, this corresponds to a yield $Y_{R-Z}$= 0.0376 liter$_{β-IP}$/h/liter$_{solution}$.

Apart from the fact that the space-time yield is low and the accumulation of secondary products is considerable, the catalyst and distillation residue are not easily separated in the homogeneous catalyst system used. It is therefore essential to discard material from time to time, as otherwise the temperature in the bottom of the distillation column would rise excessively. Thus a "monitoring" of the temperature is necessary.

According to D6, the isomerization in the liquid phase is carried out at temperatures of around 200° C. The catalyst used is silica gel with or without addition of alkyl-substituted imidazolines corresponding to the following formula.

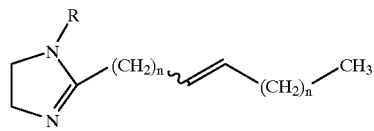

Typical experimental conditions: 300 g α-IP and 25.7 g SiO₂ are distilled for 52 h in the presence of special steel; this results in the recovery of 230 g β-IP (=76.6% yield) with 99.9% purity. Based on the quantity of catalyst used and the time, this result corresponds to a yield Y=0.174 liters β-IP per liter of catalyst per hour.

But the preparation of the organic bases is costly and the space-time yield of the process is low; with a typical value of Y=0.174 liters β-IP/liter cat/h, this process is not transferable to an industrial scale either Based on the volume of educt solution used, the yield $Y_{R-Z}$=0.0149 liter$_{β-IP}$/h/liter$_{solution}$.

The procedure described is moreover unfavorable and the absolute formation of β-IP is low. A particular disadvantage is the batchwise operation and the carrying out of the isomerization and purifying distillation of the β-IP in a single step. As a result of the high reaction temperature in the distillation apparatus, there is demonstrably a considerable reverse isomerization of β-IP to α-IP.

SUMMARY OF THE INVENTION

In view of the prior art cited and discussed above, an object of this invention is to avoid the above-mentioned disadvantages of the previous methods and to offer a process whereby 3,5,5-trimethylcyclohexa-3-en-1-one can be prepared from its isomer 3,5,5-trimethylcyclohexa-2-en-1-one in an industrially advantageous manner. In particular, a particular object of the invention is to provide an improved catalytic process in the liquid phase with a lowering of the high quantities of catalyst used hitherto.

These objects and other objects not individually stated are achieved in a process of the above-mentioned type, without the necessity of adding further organic bases.

The salt-like catalysts used are in particular alkali metal oxides, alkali metal hydroxides and alkaline earth hydroxides, hydrogen carbonates, carbonates, cyanides fluorides, bromides, alcoholates, sulfides, hydrogen sulfides, hydrogen sulfates, mercaptides, enolates, carboxylates, hydrides, complex hydrides, amides or corresponding alkali metal compounds and alkaline earth compounds which contain a carbanion as counterion, or the metallic elements directly. The above-mentioned compounds may optionally also be added in the form of solutions, with water as well as organic compounds being suitable solvents. Preferably the alkali metal compounds are used.

The achievements gained through the invention are that the space-time yield in the preparation of β-isophorone by isomerization of α-isophorone is significantly increased, the quantity of catalyst used is lowered drastically and at the same time an in principle known process is considerably simplified.

The process according to the invention renders possible a high conversion within the range of approximately 422.15 kg β-isophorone per kg of catalyst used and per hour (illustrative calculation: 0.2 mmol K₂CO₃=27.642 mg for 1 mol α-IP=138.21 g/mol: i.e. 200.00 mg potassium carbonate for 1 kg IP at 74 g β-IP/h/liter =80.43 g β-IP/h/kg solution) and thereby surpasses by far the processes known hitherto in prior art. In addition, according to the invention the accumulation of secondary products is decreased and there is an improved space-time yield $Y_{R-Z}=80$ g β-IP/h per kg α-IP, based on the volume of the educt solution used. Viewed altogether, the use of the salts and organometallic compounds according to the invention as catalysts is advantageous in every case.

In the present invention a process is used wherein α-isophorone is converted to its isomer β-isophorone, with alkali metal salts and organometallic compounds in particular being used as catalysts in the liquid phase.

A particularly advantageous procedure is one wherein the reaction and the isolation of the product do not take place in the same apparatus. The space-time yield can be significantly increased by first of all producing a mixture of α-IP and β-IP in an isomerization unit and then carrying out the purifying distillation under vacuum, as during a concentration of β-IP at normal pressure and at the boiling temperature of 186° C. there occurs a partial reverse isomerization and formation of secondary products, which is prevented by rapid removal of the reaction mixture from the reaction space. In the simplest case, the mixture consisting of the salt-like catalyst and α-IP is placed in a vessel and this mixture is thermally decomposed in a reaction tube or reactor at a suitable temperature. The reaction product contains the mixture of α-IP and β-IP corresponding to the equilibrium concentration appropriate to the given residence time and temperature. The β-isophorone thus formed is separated off by distillation; unreacted α-isophorone together with the catalyst are returned to the reaction tube or reactor, with replenishment by fresh α-IP.

In another procedure appropriate for the process according to the invention, the mixture of catalyst/α-IP is placed in an isomerization reactor and a top product having the composition of up to 50 wt. % β-IP in α-IP is withdrawn through a distillation column and then separated in a further column in such a way that pure β-IP is withdrawn as top product. The unreacted α-IP is again passed to the isomerization reactor.

The catalysts used for the purpose of the invention are the above-mentioned salts of an element of groups Ia and IIa of the periodic system. The classification of the main groups and subgroups of the periodic system of the elements is in accordance with the description in IUPAC, Pure and Appl. Chem., 66, 2423–2444,1994. Thus the metals Li, Na, K, Rb, Cs belong to group Ia and the elements Be, Mg, Ca, Sr, Ba belong to group IIa.

The compounds which can be used according to the invention as salt-like catalysts include the oxides of group Ia, and the hydroxides, hydrogen carbonates, carbonates, fluorides, bromides, alcoholates, sulfides, hydrogen sulfides, hydrogen sulfates, mercaptides, enolates, carboxylates, hydrides, complex hydrides, amides of the elements of groups Ia and IIa or corresponding alkali metal compounds and alkaline-earth metal compounds which contain a carbanion as counterion, the metallic elements and other catalytically active alkali-metal salts and alkaline-earth salts of groups Ia and IIa which possess a singly or multiply negatively charged anion as counterion Among these counterions, cyanides, halides (without chlorides), hydrogen sulfates and others are also catalytically active. The metallic elemental compounds can also be used as catalyst sources, which form the catalytically active species in situ with α-IP and with secondary products contained in α-IP. Organometallic bases include those compounds of the alkali metals and alkaline-earth metals in which the counterion is a carbanion. $sp^3$-, $sp^2$-, and sp-hybridized carbanions are among the carbanions which can be used in the invention. Without claiming to be exhaustive, one may mention the following compounds as sources of catalysts of the isomerization: alkali metal compounds and alkaline-earth metal compounds, methyl, ethyl, sec. propyl, propyl, n-butyl, phenyl, tolyl, benzyl, cyclopentadienyl compounds. Representatives of the $sp^2$- and $sp^3$-hybridized carbanions which may be mentioned are vinyllithium and sodium acetylide. By the term amides are meant the metal salts of the metals according to the invention with primary and secondary amines. Here sodium amide and sodium succinimide may be mentioned as representatives of this class of compounds.

The present invention also provides that other organometallic compounds of the above-mentioned elements having a $pK_B$ value of >5 which are basic within the stated concentration range and under the given conditions can also be used as catalysts of the reaction.

The alcoholates and mercaptides which can be used within the limits of the invention are compounds derived from the common aliphatic alcohols and mercaptans, such as methanol, ethanol or tert butanol and others, and besides these also include the phenolates and their derivatives.

Of the above-mentioned catalysts, those which contain an element of group Ia of the periodic system are particularly preferred.

Within the limits of the invention, the use of carbonates and hydroxides of lithium, sodium or potassium is most preferred.

In a further preferred development of the process according to the invention, the alkali metals and alkaline-earth metals are preferably used as elements.

In this variant, the use of metallic lithium, sodium and potassium is particularly preferred.

Most particularly preferred bases include sodium carbonate or potassium carbonate or the corresponding hydroxide compounds.

The quantity of the catalyst used is per se not particularly crucial and can therefore be varied over a wide range. It is preferred that the base be used in a quantity of from 0.0001 to 5 mol.% (mol/mol), based on the α-isophorone used.

In a particularly preferred variant of the procedure, the process according to the invention is characterized in that the catalyst is used in a proportion of between 0.001 and 5 mol.% (mol/mol), based on α-isophorone used.

In yet another particularly preferred embodiment, the proportion of catalyst to α-isophorone is within the range between 0.01–2 mol.%.

The process according to the invention is carried out within a temperature range from 100° to 400° C. The temperature range is preferably from 100° to 260° C., in particular from 150° to 250° C.

The addition of a diluent or solvent is possible, but not necessary.

The reaction is carried out preferably at a pressure of from 10 mbar to 3 bar excess pressure. Particularly favorable isomerization conditions are ~100 mbar to normal pressure (about 1 hPa) in combination with the boiling temperature of the α-isophorone.

In a particularly preferred procedure, the process according to the invention is operated continuously. In another preferred embodiment, isomerization and purifying distillation are separated from one another. After having been separated off, the liquid phase containing the isomerizate is distilled under vacuum in order to separate α-isophorone and β-isophorone.

The distillation takes place at temperatures at which the thermally induced reverse isomerization is largely ruled out.

Here it is found advantageous to recirculate the bottom product of the distillation into the isomerization step.

The feed of fresh α-isophorone into the isomerization is regulated in such a way that that the volume separated off as β-IP is compensated for. Depending on the β-IP space-time yield, up to 10 vol.% of fresh α-IP may be introduced into the isomerization in this way.

The volumetric flow rate of recirculated α-IP from the purifying distillation, depending on the conditions, can be up to 90 vol.%, based on the original volume of the isomerization solution.

A β-IP content of from 1% to 50% β-IP/α-IP, depending on the procedure, is established at the top of the isomerization unit. This mixture is then subjected to a vacuum distillation, whereby a β-IP product having a purity of >97% is obtained. The bottom product in the column is returned to the isomerization unit without further purification.

The new process is also distinctly superior to the prior art with regard to the accumulation of secondary products (in comparison e.g. with D1, where stoichiometric quantities of Grignard compound are used) and to the space-time yield based on the volume of the educt solution. Through the use of a salt-like or organometallic catalyst in the concentration range of $10^{-4}$ to 10 mol.% relative to α-IP used in the isomerization volume, selectivities of >99% are achieved, whereby the formation of high boilers can be significantly decreased as compared with the processes described in prior art.

DETAILED DESCRIPTION OF THE PREFERRED EMBODIMENTS

EXAMPLE 1

Commercially available, technical sodium carbonate is used as the basic catalyst for the isomerization. The apparatus for carrying out the isomerization consists of a mushroom-shaped heater, an isomerization flask with attached distillation column, through which a primary mixture composed of α-IP and β-IP is withdrawn, and a pump for recirculating the unreacted α-isophorone left after the purifying distillation of β-IP. 800 ml of technical α-isophorone is placed in a receiver (firm Atochem >98%; =723 g) and a quantity of sodium carbonate corresponding to the values given in the Tables is stirred in. The suspension is heated to boiling point at normal pressure and the quantity of the α-IP delivered by a Telab pump is coordinated with the quantity of the distillate withdrawn. At a constant withdrawn volume of 25 vol.% relative to α-IP used, and at a constant reflux ratio of the primary distillation, the following rates of formation of high boilers*, rates of formation of β-IP and β-IP selectivities are found as a function of various concentrations of catalyst:

| Mol. % $Na_2CO_3$ [mol. % per mol α-IP] | Rate of formation of HB* [g HB/h/liter α-IP] | Rate of formation of β-IP [g β-IP/h/liter α-IP] | Selectivity β-IP |
|---|---|---|---|
| $2 \times 10^{-2}$ | 0.6 | 47.4 | 96.3 |
| $2 \times 10^{-1}$ | 0.6 | 63.5 | 99.1 |
| $2 \times 10^{-0}$ | 1.7 | 72 | 97.7 |

*HB: high boilers = collective term for secondary products of the isomerization

The temperature at the bottom of the isomerization column remains constant during the reaction period. The primary distillate obtained is conveyed to a distillation column operating at a partial vacuum of 5 mbar to 100 mbar. The top product obtained at 12 mbar has a boiling point of 55° to 58° C. and consists to the extent of >99% of β-isophorone. At the given scale of the experiment, 47.4 to 72 g β-isophorone is formed per hour and per liter volume of α-IP in the isomerization reactor. The bottom product consisting of unreacted α-isophorone is returned to the isomerization reactor. The calculated yield based on the quantity of catalyst used, $Y_{\beta\text{-}IP}$, is 229.7 kg β-IP/h/$kg_{cat.}$ in a continuous operation and at 0.2 mol.% (=0.2764 g cat./mol IP) catalyst concentration. Based on the volume of the solution being isomerized, the space-time yield $Y_{R\text{-}Z}$=0.0635 $liters_{\beta\text{-}IP}$/h/$liter_{Solution}$.

EXAMPLE 2

Technical sodium hydroxide in various concentrations is stirred into α-IP in the apparatus already described above. With the identical continuous procedure (see Example 1), at the top of the isomerization unit a withdrawal rate of 25 vol.% of a primary distillate is established, based on the quantity of isomerization and the reflux ratio. The use of HPLC to quantify the rate and selectivity of the β-IP formation produces the following results:

| Mol. % NaOH [mol. % per mol α-IP] | Rate of formation of HB* [g HB/h/liter α-IP] | Rate of formation of β-IP [g β-IP/h/liter α-IP] | Selectivity β-IP |
|---|---|---|---|
| $2 \times 10^{-2}$ | 0.5 | 54.6 | 99.1 |
| $2 \times 10^{-1}$ | 35.4 | 79.5 | 69.2 |

*HB: high boilers = collective term for secondary products of the isomerization

The activity of the catalyst remains unchanged throughout the course of the experiment.

EXAMPLE 3

Technical potassium carbonate in various concentrations is stirred into α-IP in the apparatus already described above. With the identical continuous procedure (see Example 1), at the top of the isomerization unit a withdrawal rate of 25 vol.% of a primary distillate is established, based on the quantity of isomerization and the reflux ratio. The use of HPLC to quantify the rate and selectivity of the β-IP formation produces the following results.

| Mol. % $K_2CO_3$ [mol. % per mol α-IP] | Rate of formation of HB* [g HB/h/liter α-IP] | Rate of formation of β-IP [g β-IP/h/liter α-IP] | Selectivity β-IP |
|---|---|---|---|
| $2 \times 10^{-2}$ | 0.9 | 73.8 | 98.9 |
| $2 \times 10^{-1}$ | 26.3 | 76.4 | 74.4 |
| $2 \times 10^{-0}$ | 57.2 | 68.8 | 54.6 |

*HB: high boilers = collective term for secondary products of the isomerization

The activity of the catalyst remains unchanged throughout the course of the experiment.

EXAMPLE 4

Various catalysts containing alkali-metal cations are compared with regard to their catalytic activity during the isomerization under conditions corresponding to those in the previous Examples.

| Mol. % base [mol. % per mol α-IP] | Rate of formation of HB* [g HB/h/liter α-IP] | Rate of formation of IP [g β-IP/h/liter α-IP] | Selectivity β-IP |
|---|---|---|---|
| $2 \times 10^{-2}$ LiOH | 3.0 | 61.3 | 95.3 |
| $2 \times 10^{-2}$ $Li_2CO_3$ | 0.4 | 48.3 | 99.2 |

-continued

| Mol. % base [mol. % per mol α-IP] | Rate of formation of HB* [g HB/h/liter α-IP] | Rate of formation of IP [g β-IP/h//liter α-IP] | Selectivity β-IP |
|---|---|---|---|
| 2 × 10⁻²KOH | 3.9 | 66.9 | 94.5 |
| 2 × 10⁻² Na(OMe) | 0.7 | 46.9 | 98.5 |

*HB: high boilers = collective term for secondary products of the isomerization

EXAMPLE 5

Various alkali-metal bases and alkaline-earth bases used as catalysts are compared with regard to their catalytic activity during the isomerization under conditions corresponding to those in the previous Examples.

| Mol. % base [mol. % per mol α-IP] | Rate of formation of HB* [g HB/h/liter α-IP] | Rate of formation of β-IP [g β-IP/h/liter α-IP] | Selectivity β-IP |
|---|---|---|---|
| 2 × 10⁻²Ca(OH)₂ | 0.4 | 41.1 | 96.7 |
| 2 × 10⁻²NaH | 0.8 | 58.6 | 96.6 |
| 2 × 10⁻²Mg(OH)₂ | 0.8 | 8.2 | 91.5 |
| 2 × 10⁻¹Mg(OH)₂ | 0.7 | 9.3 | 93.3 |

*HB: high boilers = collective term for secondary products of the isomerization

EXAMPLE 6

1 mol.% of sodium carbonate is used as the basic catalyst of the isomerization under the conditions described above. A space-time yield (per hour and quantity of catalyst used) Y=15.357 kg β-IP/h/kg catalyst is achieved. This corresponds to a space-time yield $Y_{R-Z}$=0.086 kg β-IP/h/liter, based on α-IP used [liter α-IP]. The rate of formation of high boilers, quantified by HPLC, is 1.1 g HB/h/l. This corresponds to a selectivity of β-IP formation of 98.8%.

EXAMPLE 7

Various catalysts containing alkali-metal cations are compared with regard to their catalytic activity during the isomerization under conditions corresponding to those in the previous Examples.

| Mol. % base [mol. %/ mol α-IP] | pKa* | Rate of formation of HB**[g HB/h/liter α-IP] | Rate of formation of β-IP[g β-IP/h/liter α-IP] | Selectivity β-IP |
|---|---|---|---|---|
| 2 × 10⁻² NaNH₂ | 36 | 1.0 | 49.6 | 97.9 |
| 2 × 10⁻² NaHCO₃ | 64 | 0.8 | 55.1 | 98.6 |
| 2 × 10⁻² KHCO₃ | 6.4 | 3.0 | 64.4 | 95.5 |
| 2 × 10⁻² Na(CH₃CO₂) | 4.8 | 0.7 | 49.2 | 98.7 |

*pka data refer to the basicity of the anion in equilibrium with the corresponding protonated step
**HB: high boilers = collective term for secondary products of the isomerization

EXAMPLE 8

Various catalysts containing alkali-metal cations are compared with regard to their catalytic activity during the isomerization under conditions corresponding to those in the previous Examples.

| Mol. % base [mol. %/ mol α-IP] | pka* | Rate of formation of HB**[g HB/h/liter α-IP] | Rate of formation of β-IP [g β-IP/h/liter α-IP] | Selectivity β-IP |
|---|---|---|---|---|
| No catalyst | / | 0 | 8.0 | 100 |
| 2 × 10⁻² kHSO₄ | −5.2 | 0.7 | 44.7 | 98.5 |

*pKa data refer to the basicity of the anion in equilibrium with the corresponding protonated step
**HB: high boilers = collective term for secondary products of the isomerization

EXAMPLE 9

Various catalysts containing alkali-metal cations and the elements are compared with regard to their catalytic activity during the isomerization under conditions corresponding to those in the previous Examples.

| Mol. % Na₂CO₃ [mol. % per mol α-IP] | Rate of formation of HB* [g HB/h/liter α-IP] | Rate of formation of IP [g β-IP/h/liter α-IP] | Selectivity β-IP |
|---|---|---|---|
| 2 × 10⁻²LiAlH₄ | 0.8 | 43.3 | 98.3 |
| 2 × 10⁻²LiBH₄ | 0.8 | 46.1 | 98.3 |
| 2 × 10⁻²Na | 0.7 | 53.7 | 98.7 |

Comparative Example 1

If the procedure described in the Japanese Offenlegungsschrift (A) HEI 1-175954 is followed (300 g α-IP;25.7g SiO₂, withdrawal rate 5 g/h) and an 89% β-IP/α-IP mixture is withdrawn per hour using SiO₂ as catalyst, then, based on the quantity of catalyst, the yield Y=0.174 $kg_{β-IP}$/h/$kg_{cat}$. Based on the educt solution used, the space-time yield $Y_{R-Z}$=0.0149 $liters_{β-IP}$/h/$liter_{solution}$.

What is claimed is:

1. A process for the preparation of 3,5,5-trimethylcyclohexa-3-en-1-one (β-isophorone) by isomerizing 3,5,5-trimethylcyclohexa-2-en-1-one (α-isophorone) in the presence of a catalyst, without addition of another organic base, at 100° to 260° C. in a liquid phase, comprising:
    using at least one member selected from the group consisting of elements of groups Ia or IIa and salts of elements of group Ia as the catalyst.

2. The process according to claim 1, wherein:
    the catalyst comprises at least one member selected from the group consisting of alkali metal oxides, alkali metal hydroxides, carbonates, hydrogen carbonates, hydrides, complex hydrides, amides, alcoholates, mercaptides, carboxylates, bromides, fluorides, cyanides, hydrogen sulfides, hydrogen sulfates, sulfides, or organometallic alkali metal compounds, and mixtures thereof.

3. The process according to claim 2, wherein:
    the catalyst comprises at least one member selected from the group consisting of alkali metal carbonates, and alkali metal hydroxides and.

4. The process according to claim 3, wherein the catalyst comprises at east one member selected from the group consisting of hydroxides and carbonates of sodium and potassium.

5. The process according to claim 1, comprising:
    using the catalyst in a proportion of 10⁻⁴ to 5 mol. %, based on α-isophorone.

6. The process according to claim 5, comprising:
using the catalyst in a proportion of $10^{-3}$ to 5 mol. %, based on α-isophorone.

7. The process according to claim 6, comprising:
using the catalyst in a proportion of 0.01 to 2 mol. %, based on α-isophorone.

8. The process according to claim 1, comprising isomerizing at normal pressure (about 1 Pa and at boiling temperature of α-isophorone.

9. The process according to claim 1, comprising:
operating the process continuously.

10. The process according to claim 9, comprising:
recirculating bottom product of the distillation, which contains active catalyst and unreacted α-isophorone, into the isomerization step.

11. The process according to claim 1, comprising:
isomerizing at a temperature of from 150° to 250° C. and at a corresponding pressure maintaining a liquid phase, withdrawing reaction mixture continuously, distilling the withdrawn reaction mixture at a pressure of 100 to $3 \times 10^4$ Pa; and optionally returning product at the bottom of the distillation column to the isomerizing step.

12. The process according to claim 3, wherein the alkali metal carbonates are lithium, sodium or potassium carbonates.

13. The process according to claim 3, wherein the alkali metal hydroxides are lithium, sodium or potassium hydroxides.

14. The process according to claim 1, wherein the elements of groups Ia are metallic lithium, sodium or potassium.

* * * * *